United States Patent [19]

Frick

[11] 4,425,173

[45] Jan. 10, 1984

[54] APPARATUS AND METHOD FOR PRODUCING AN ELASTICIZED GARMENT

[75] Inventor: Richard H. Frick, Winnebago County, Wis.

[73] Assignee: Kimberly-Clark Corporation, Neenah, Wis.

[21] Appl. No.: 399,559

[22] Filed: Jul. 19, 1982

[51] Int. Cl.³ .................... A61F 13/16; B32B 31/08; B32B 31/12

[52] U.S. Cl. .................... 156/204; 112/132; 112/414; 156/164; 156/205; 156/270; 156/303; 156/471; 156/474; 156/522; 156/551; 156/554; 223/38

[58] Field of Search ............... 156/163, 204, 205, 267, 156/303, 470, 471, 474, 495, 522, 551, 554, 270; 112/132, 413, 414; 223/38

[56] References Cited

U.S. PATENT DOCUMENTS

| | | | |
|---|---|---|---|
| 1,606,900 | 11/1926 | Rockwood | 112/414 |
| 2,179,842 | 11/1939 | Collins | 156/204 |
| 2,632,495 | 3/1953 | Agee | 156/471 |
| 2,874,408 | 2/1959 | Uieli et al. | 156/470 |
| 3,086,685 | 4/1963 | Cahill | 156/474 |
| 3,157,551 | 11/1964 | Granozio | 156/471 |
| 3,791,266 | 2/1974 | Bucalo | 156/204 |
| 3,804,688 | 4/1974 | Hillenbrand et al. | 112/132 |
| 3,912,573 | 10/1975 | Kunz | 156/471 |
| 4,227,952 | 10/1980 | Sabee | 156/204 |

FOREIGN PATENT DOCUMENTS 927711   6/1963   United Kingdom ............... 156/462

Primary Examiner—Jerome W. Massie
Attorney, Agent, or Firm—Richard C. Ruppin

[57] ABSTRACT

An apparatus and method for elasticizing the leg areas of a conformable garment is disclosed in which a continuous length of web material is continuously fed onto a moving support surface. As the web is fed onto the support surface, oscillating means moves the web in alternating directions in the direction of movement of and opposite to the direction of movement of the web as a whole to form spaced apart relatively flat folds in the web. Continuous, moving elastic ribbon is applied and adhered to the web in a tensioned condition across the folds, the folds are at least partially opened and the elastic is severed opposite the partially opened folds to provide discrete elastic strips attached at desired locations to the web.

11 Claims, 3 Drawing Figures

APPARATUS AND METHOD FOR PRODUCING AN ELASTICIZED GARMENT

FIELD OF THE INVENTION

This invention relates to an apparatus and method for forming conformable garments having selected discrete elasticized areas and, more particularly, to an apparatus and method for elasticizing only the leg areas of disposable diapers on a high speed production basis.

BACKGROUND OF THE INVENTION

Due to the improved fit and fluid sealing properties provided by leg elasticization, manufacturers of disposable diapers have, in recent years, developed various methods and apparatus for attaching elastic strips to the leg areas of the diapers. Because of the high speed, continuous nature of diaper manufacturing methods, virtually all of the commercially practicable processes have utilized a continuous elastic ribbon affixed to the diaper in the leg areas and subsequently cut either prior to or as a part of the severing of the continuous web into separate diapers. Typical of these processes and apparatus is that disclosed in U.S. Pat. No. 4,081,301 to Buell. This patent discloses adhering of the continuous elastic ribbon only in discrete, intermittent areas corresponding to the leg areas in a finished diaper. After adhering of the ribbon to a continuous web, the ribbon and the web are simultaneously cut at what will be the waist of the diaper when the manufacturing process is finished. The drawback of this process is that it is inefficient from the material use aspect in that it leaves an unneeded length of elastic attached to the diaper. Another approach to handling the problem is disclosed in U.S. Pat. No. 4,227,952 to Sabee. In the method of this patent, the elastic ribbon is continuously applied to the web, however, before the attachment of the ribbon to the web, the latter is tucked in the areas of the web corresponding to the waist areas of the finished diapers. Consequently, the elastic ribbon is attached to the web only in the leg areas of the finished diaper. The elastic ribbon is then severed at the points opposite the tucked areas of the web and the web is then untucked so that elastic is only in the leg areas of the finished diaper and the waist areas contain no unneeded elastic. The problem with this method and the apparatus used in it is that it is difficult to operate at the high speeds required for commercial usefulness. Much of the difficulty of the Sabee approach is due to the attempt to intermesh, in gear wheel fashion, projecting tucking members with members defining receptacles to form tucks in the web. Intermeshing of these members in this manner is too abrupt and presents positioning difficulties which prevent high speed operation and places too much stress on the web. Also, the depth of the tuck is limited by the width of the receptacle openings through which the tucking members must rotate to form the tucks.

A second approach using a tucking method is that disclosed in U.S. application Ser. No. 181,281, filed Aug. 27, 1980. The apparatus and method of this application solves the intermeshing difficulties of Sabee by mounting the projecting tucking members on a conveyor chain in a manner such that they are moveable relative to the conveyor chain in the direction of their length. The movement of the tucker members into the tuck defining receptacles is caused by cam means connected to the tucker members so that the rate of insertion of the tucker members into receptacles and the position at which they are inserted is controlled relatively independently of the position and movement of the conveyor chain carrying the tucker members. However, this approach has the problems of considerable complexity resulting in high initial cost of the apparatus and substantial wear requiring constant maintenance and adding further to the overall cost.

It is a principal object of this invention to provide, for use in a high speed production process and apparatus, a relatively simple, efficient method and apparatus for attaching a continuously moving elastic ribbon to a continuously moving web such that only selected discrete areas of a finished conformable garment fabricated from the web will be elasticized. The conformable garment may be a disposable diaper in which only the areas of the web corresponding to the leg areas in finished diapers will be elasticized. It is a particular object of this invention to provide a method and apparatus for forming folds in a continuously moving web utilizing a relatively simple apparatus and method which eliminates the need for complex intermeshing folding mechanisms.

The invention is accomplished by supplying a continuous moving web on to moving support surface, folding the web against itself at spaced intervals as it is supplied to the moving surface, moving a continuous length of elastic ribbon into engagement with the folded web across the folds, at least partially opening the folds in the web, and severing the elastic across the open folds. The web is folded as it moves on to the support surface by an oscillating means which moves alternately in directions with and opposite to the direction of movement of the web as a whole. Because the web is not supported to hold the walls of each fold apart, each fold will have a thickness on the support surface equal to the total thickness of the fold layers, that is, the total thickness of the fold walls and any other web portions engaging the fold walls.

DESCRIPTION OF THE DRAWINGS

Further objects and advantages of the invention will appear when taken in conjunction with the accompanying drawings in which.

DETAILED DESCRIPTION OF THE INVENTION

Figure 1:
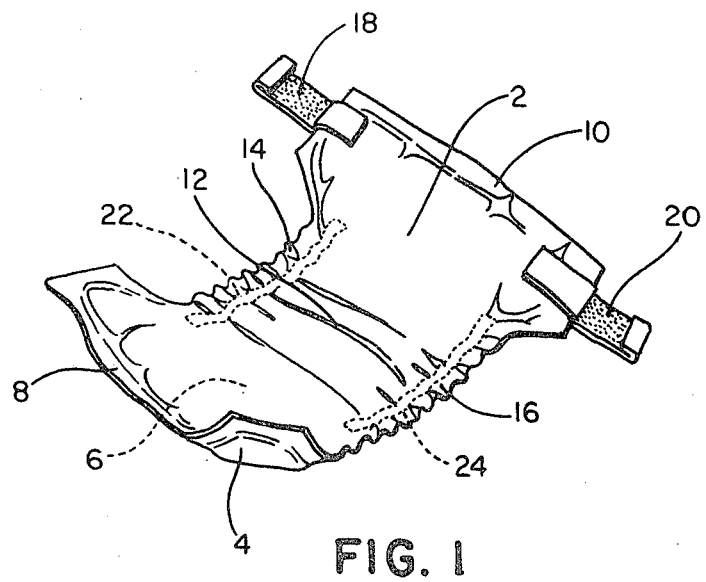
FIG. 1 is a perspective view of a finished elasticized leg disposable diaper just prior to its fitting onto a wearer.
Figure 2:
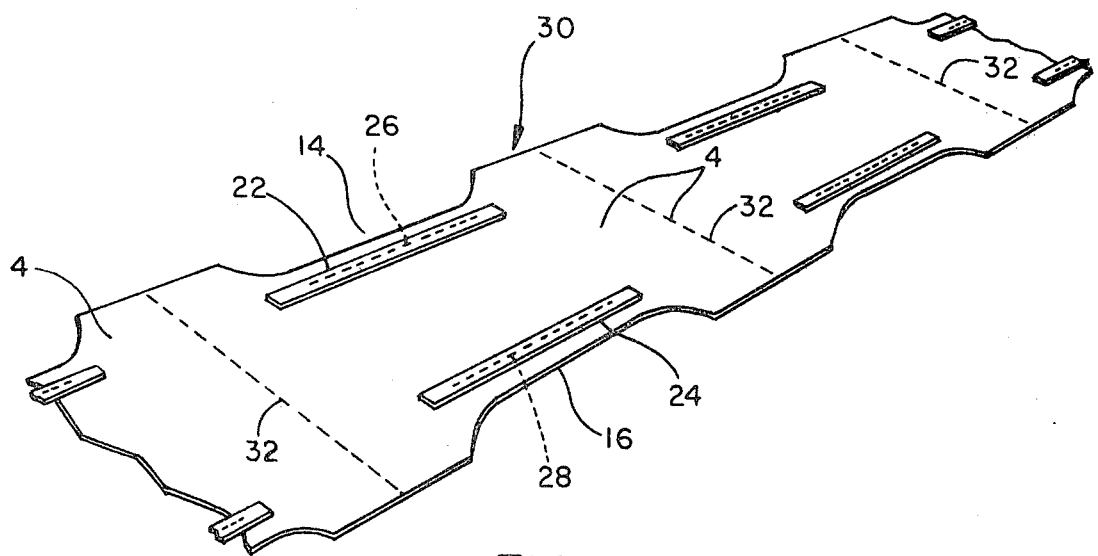
FIG. 2 is a perspective view showing the web from which disposable diapers are formed after elastic strips have been applied for providing leg elasticization.

For purposes of background, the elasticized leg disposable diaper produced by the apparatus and method of the invention will first be discussed. Referring to FIGS. 1 and 2, there is shown in FIG. 1 a disposable diaper having a topsheet 2 and a backsheet 4, a front waist area 8, a rear waist area 10, and a crotch area 12 intermediate the two waist areas. Leg areas 14 and 16 are positioned laterally of the crotch area 12 and intermediate of the waist areas 8 and 10. Waist fastening tapes 18 and 20 are bonded to the corner areas of the rear waist area 10 and are fastenable to the front waist area 8 when the diaper is fitted to a wearer to secure the diaper on the wearer. Elastic strips 22 and 24 are attached substantially parallel to the length of a diaper in the leg areas 14 and 16 respectively, as shown in FIG. 2, to elasticize the leg areas of the diaper and provide a snug fit around the legs of the wearer. In FIG. 1, the elastic strips 22 and 24 are shown in a relaxed condition in which they cause random pleating or folding of the topsheet 2 and backsheet 4.

In FIG. 2, a web 30 is shown with the backsheet 4 of each diaper which is eventually cut from the web 30 being separately identified by the dashed lines 32. The elastic strips 22 and 24 are attached to each backsheet 4 by adhesive lines 26 and 28, respectively. The backsheet 4 and the elastic strips 22 and 24 are shown in an extended, flat condition in which the elastic strips 22 and 24 are stretched. The leg areas 14 and 16 have previously been cut from the web.

Figure 3:
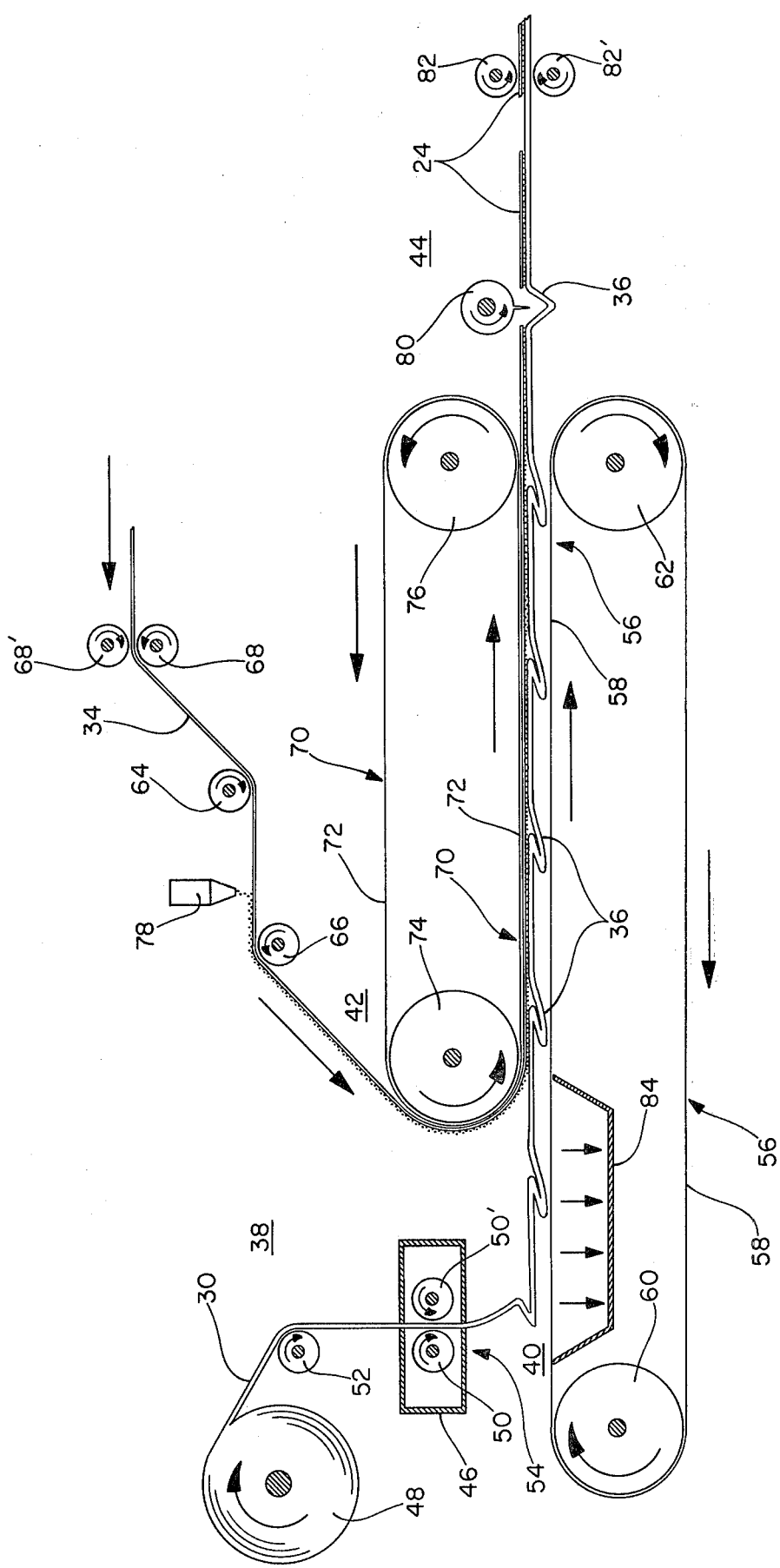
FIG. 3 is a simplified side elevation, cross-sectional view showing the apparatus utilized in the invention.

With reference to FIG. 3, an apparatus is shown for supplying the web 30 from a web supply section 38, folding the web 30 at a folding section 40, supplying and attaching elastic ribbons 34 to the web 30 at section 42, partially opening the web 30 and cutting the elastic ribbons 34 opposite the location of the partially open folds 36 at the unfolding and cutting section 44, and finishing the unfolding of the web 30. Apparatus for applying the absorbent pads 6, the waist fastening tapes 18 and 20, and the topsheet 2, all illustrated in FIG. 1, is not shown or described herein inasmuch as they form no part of the present invention and may be incorporated into the finished diaper by methods and apparatus that are well known in the art. Also, in the view of FIG. 3, various elements of the apparatus illustrated correspond to identical elements which are directly behind the illustrated elements and are not shown. Inasmuch as a description of such identical elements is not necessary for an understanding of the present invention, they will not be discussed herein.

With reference to FIG. 3, at the web supply section 38, the web material 30 is drawn over a tension roll 52 from a supply roll 48 by feed rolls 50, 50'. The web 30 is fed to the folding section 40 at the feed end of the apparatus where folds 36 are formed in the web 30 by folding means 54. The web 30, as folds 36 are formed therein, is fed onto a conveyor means 56 which comprises a continuous, moving perforated belt or screen carried on rolls 60 and 62, one of which is driven by a suitable motive source (not shown). At the elastic ribbon supply and application section 42, the elastic ribbons 34 are drawn from supply rolls (not shown) by feed rolls 68, 68'. The elastic ribbons 34 are then passed between tension sensing rolls 64 and 66 and under nip means 70 as the ribbons are applied to the web 30. The nip means 70 includes a belt 72 mounted on and continuously rotated by rolls 74 and 76, one of which is driven by a suitable motive source (not shown).

A feedback means (not shown) controls the speed of the feed rolls 68, 68' such that the elastic ribbons 34 are applied to the web 30 under tension. The effect of applying the elastic ribbons under tension to the web 30 is to elasticize those portions of the diapers obtained from the web 30 after the cutting of the web. Prior to application of the elastic ribbons 34 to the web 30, adhesive applicator means 78 applies at least one line of adhesive to each of the ribbons 34 to permit adhering of the ribbons 34 to the web 30 as they pass under the nip means 70. Note, however, that other materials and methods or means may be used to bond or adhere the elastic ribbons 34 to the web 30. For example, energy may be applied to the ribbons 34 to cause their bonding to the web 30 or the ribbons 34 may be of an elastic material which itself adheres to the web 30.

At the cutting and unfolding section 44, the web 30 is at least partially unfolded and the ribbons 34 are severed opposite the partly opened folds 36 by cutting means 80. The folds 36 are partially opened or unfolded by drive rolls 82, 82' which, after the severing of the ribbon 34, also extend the web and entirely remove the folds 36 from the web 30 due to their rotating at a higher lineal speed than the lineal speed of the web as it passes between the nip means 70 and the conveyor means 56. The continuous web 30 with the spaced apart elastic strips 22 and 24, as shown in FIG. 2, then continue on to additional sections in the diaper producing apparatus.

Referring again to the folding section 40 as shown in FIG. 3, the folding means 54 includes the feed rolls 50, 50' between which the web 30 passes and an oscillating means 46. The oscillating means 46 is of a type well known in the art and accordingly will not be described in detail herein. The feed rolls 50, 50' are carried by the oscillating means 46 and move in a reciprocating or oscillating manner, preferably in directions with or opposite to the direction of general movement of the web 30 as a whole as carried by conveyor means 56. As the feed rolls 50, 50' move, as part of their oscillating motion, in the direction of general movement of the web 30, they do so at a higher speed than the movement of the web 30 such that a portion of web 30 is laid against another portion of web 30 to form a tuck 36. The feed rolls 50, 50' are then moved in a direction opposite to that of the general movement of the web 30 as a whole to return to a predetermined location at which the oscillating motion of the rolls 50, 50' will be reversed and another fold 36 will be formed in the web 30. A plurality of spaced apart folds 36 are thus formed in the web 30 as it is fed by the feed rolls 50, 50' on to the moving screen 58 and carried by the screen 58 to the nip formed by nip means 70 and screen 58. To prevent each fold 36 from unfolding upon reversal of the oscillating motion of the feed rolls 50, 50' to move in a direction opposite to that of the general movement of the web 30, vacuum means 84 is positioned beneath the folds 36 as they are formed on the screen 58 to hold them in position against such opposite movement of the feed rolls 50, 50'. It should be noted that the spacing between the belt 72 of nip means 70 and screen 58 and the spacing between the wall portions of the folds 36 are somewhat exaggerated for purposes of illustration only. In actual practice, the belt 72 presses firmly against the screen 58 to hold the folds 36 flat and to obtain good adherence of the elastic ribbon 34 to the web 30.

It will be understood that the foregoing description of the present invention is for purposes of illustration only and that the invention is susceptible of a number of modifications or changes, none of which entail any departure from the spirit and scope of the present invention as defined in the hereto appended claims.

What is claimed is:

1. In an apparatus for applying continuously moving elastic ribbon to a continuously moving web, the combination comprising:

means for supplying the web to a moving support surface;

means for transverse folding the web against itself at spaced intervals;

means for moving the elastic ribbon into engagement with the folded web across the folds;

means for adhering the elastic ribbon to the unfolded portions of the web;

means for at least partially opening the folds in the web; and means for severing the elastic ribbon across the open folds.

2. The combination according to claim 1 wherein the means for folding the web comprises oscillating means engaging and moving a portion of the web alternately in directions with and opposite to the direction of movement of the web as a whole.

3. The combination according to claim 2 wherein the oscillating means moves said portion of the web in the direction of the movement of the web as a whole at a higher rate than that of said movement as a whole.

4. The combination according to claims 2 or 3 wherein the oscillating means comprises a pair of feed rolls for moving the web.

5. The combination according to claim 2 wherein the oscillating means controls the rate of movement of the web as a whole in the direction of its length.

6. The combination according to claims 1, 2 or 3 wherein the means for opening the folds in the web comprises drive means for accelerating the rate of movement of the web after the elastic ribbon is adhered to the web.

7. A method of applying elastic ribbon strips to a continuous moving web comprising the steps of:

supplying the web to a moving support surface;

folding the web transversely against itself at spaced intervals to a thickness equal to the total thickness of the fold layers;

continuously moving a continuous elastic ribbon into engagement with the web across the folds;

moving the folded portions of the web apart to create openings between the folds; and severing the elastic ribbon across the openings to form a series of spaced apart disconnected elastic ribbon strips.

8. The method according to claim 7 wherein the step of folding the web is accomplished by oscillating the portions of the web to be folded with and against the direction of the movement of the web as a whole.

9. The method according to claims 7 or 8 further comprising the step of gripping the web at the edge of the fold in the direction of movement of the web subsequent to the making of the fold.

10. The method according to claims 7 or 8 wherein the step of folding the web includes moving the portion of the web to be folded in the direction of movement of the web as a whole at a higher rate than that of said movement as a whole.

11. The method according to claim 10 further comprising the step of gripping the web at the edge of the fold in the direction of movement of the web subsequent to the making of the fold.

* * * * *